July 1, 1969 J. A. GABRIELSEN Plant Pat. 2,898
PURPLE RASPBERRY
Filed Sept. 11, 1967
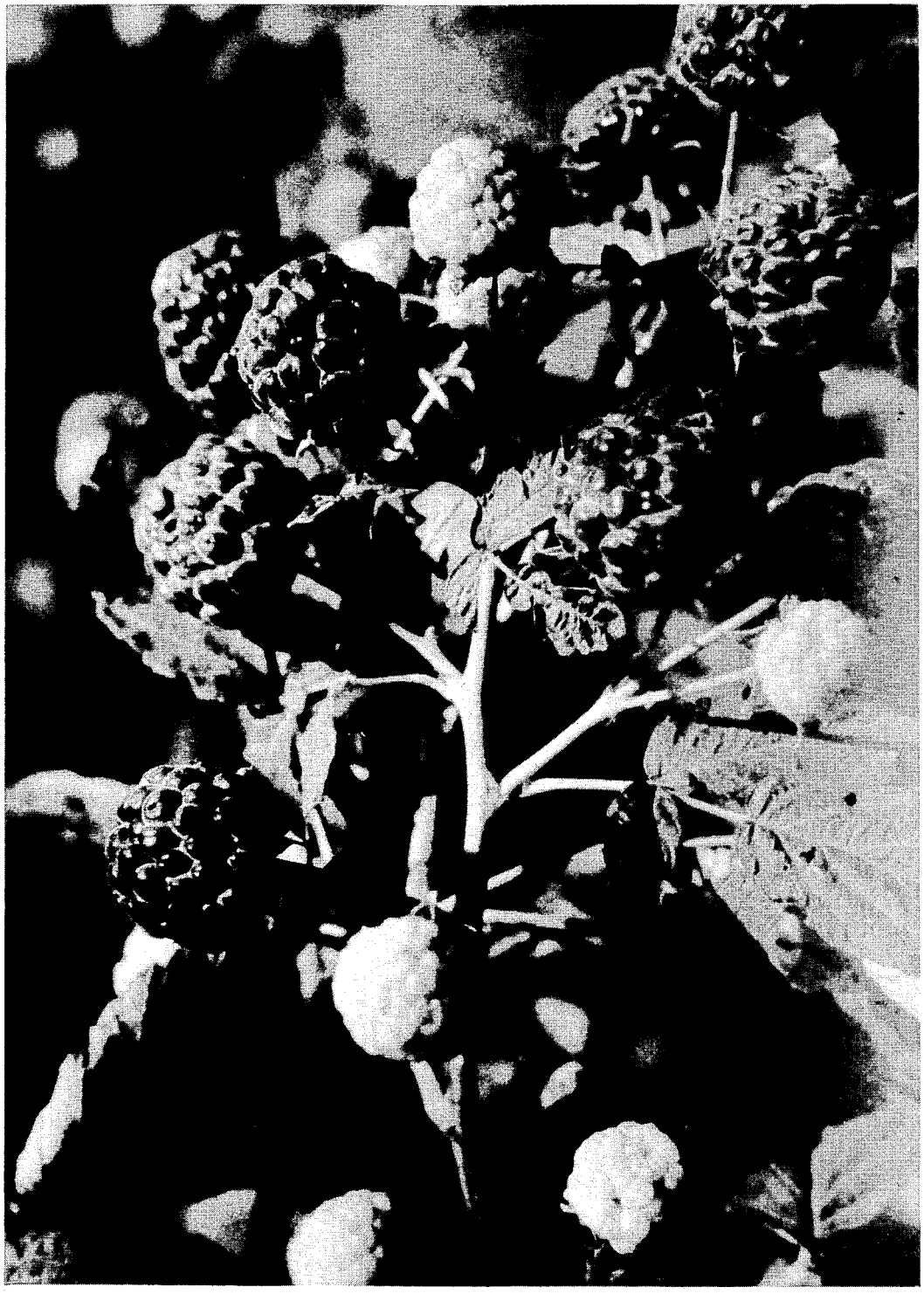

United States Patent Office

Plant Pat. 2,898
Patented July 1, 1969

2,898

PURPLE RASPBERRY

Joseph A. Gabrielsen, Graettinger, Iowa 51342

Filed Sept. 11, 1967, Ser. No. 667,613
Int. Cl. A01h *5/08*
U.S. Plt.—46 1 Claim The present invention relates to a new and distinct variety of purple raspberry plant which was discovered by me on my property at Graettinger, Palo Alto County, Iowa, having originated in a planting of the variety, "Potomac" (unpatented).

Prolonged tests and observations of my new variety have established that it is definitely distinguished from the "Potomac" variety by the much more vigorous growth of the plant; much larger size of the canes, their greater productivity than the "Potomac" variety, better resistance to hot, dry weather with fruit which is much larger, milder in flavor and not so tart as "Potomac." The new variety is definitely distinguished from all others which I am aware yet retains the desirable characteristics of "Potomac." The following characteristics are particularly outstanding in my new variety and together represent a unique and desirable combination which make my new variety especially useful for home and commercial use:

(1) The exceptional vigor, drought resistance and productivity of the plant;

(2) Canes not susceptible to anthracnose; upright, which hold fruit off the ground;

(3) The relatively large size of the fruit, constant through the picking season despite dry and hot weather;

(4) The delectable flavor of the fruit;

(5) Hardy plant which withstood 25 degrees below zero, F.

Asexual reproduction of the new variety by tipping in Palo Alto County, Iowa, shows that the foregoing characteristics and distinctions come true to form and are established and transmitted through succeeding propagations.

The accompanying drawing shows typical specimens of the fruit and foliage of my new variety.

The following is a detailed description of my new variety with color terminology in accordance with Maerz & Paul's "Dictionary of Color," as grown in Graettinger, Iowa.

Parentage: Presumed to be a bud mutation of "Potomac," but the exact origin is unknown.

Propagation: Holds its distinguishing characteristics through succeeding propagations by tipping.

Dates first and last picking: In 1967; July 14–August 7.

Season: Late, ripening with "Latham" (unpatented).

Plant:

*Growth.*—Very vigorous.

*Root.*—Very vigorous.

*Crown.*—Branched, large; from 10 to 12 canes and more.

*Leaves.*—Many, large; on young primocanes, petiole average about 3 inches in length; stout. Color: upper surface—Plate 23L–10; lower surface—Plate 29C–5. Pubescence—wanting. Three to five leaves. Size—central leaflet—4½ inches x 3 inches; shape—ovate to lanceolate, tapering to acute point at distal end. The leaves on the ends of the fruiting canes, however, are smaller, irregularly shaped and distinctly lobed. Serrations—double serrations are narrow and acute with protruding downward hooked point at apexes.

*Canes.*—Stout, erect, tall; glabrous with prickles. Thorns—moderate. Length—⅛ inch, slightly angled downward; 5 in a cylinder of cane surface one inch in length in mid-cane. Color—Floricanes, Plate 55J–1 with Lilac bloom; Primocanes, Plate 17A–5.

Fruit: Conditions when described—Prime (date July 16).

(a) *Color.*—Wineberry, Plate 55H–4 with dull, darker bloom when fully ripe.

(b) *Drupelets.*—Large, averaging about ⅛ inch in diameter; irregularly shaped with definite suture from base to base in most. Pistils 1/16 inch long and curved upward.

(c) *Size.* — Large, uniform, remaining constant throughout picking season. Length—¾ inch. Transverse diameter—13/16 inch.

(d) *Form.*—Rounded truncate; tapering slightly; uniform, flat base; rounded apex.

(e) *Cavity.*—5/16 inch diameter; deep; funnel-shaped. Color—Plate 53C–4.

(f) *Torus.*—Length—25/64 inch. Diameter—¼ inch. Necked at base, tapering bluntly to apex. Color—Amber Y, Plate 10J–3.

(g) *Sepals.*—Acuminate. Number—6. Length—⅜ inch. Width at base—⅛ inch. Tips, acute.

(h) *Flesh.*—Juicy; quite firm, meaty. Color (flesh and juice)—Garnet Red, Plate 6K–6.

(i) *Seed.*—Size—medium, about 5/32 inch, width—2/32 inch, thickness—1/32 inch. Surface-rough. Color—Garnet Red, Plate 6K–6.

(j) *Flavor.*—Subacid; rich; mildly tart.

(k) *Shipping quality.*—Good; tender when too ripe.

(l) *Eating quality.*—Very good fresh or frozen.

(m) *Picking quality and adherence.*—Detaches easily when ripe but does not fall off torus. The upright habit of sturdy canes keeps fruit off ground.

Drought resistance: Exceptionally resistant to drought and high temperatures, determined by comparison with other varieties grown in same location.

Soil where grown: Black loam with clay subsoil; well drained.

Culture: Cultivated; unsprayed.

I claim:

1. A new and distinct variety of purple raspberry plant, substantially as herein shown and described, characterized particularly as to novelty by its exceptional vigor, productivity, heat and drought resistance, canes, not susceptible to anthracnose, hardy; withstanding 25 below zero F. Without injury, the delectable flavor of its fruit, and by the relatively large and constant size of fruit even under unfavorable weather conditions.

No references cited.

ROBERT E. BAGWILL, *Primary Examiner.*